US010920833B2

(12) United States Patent
Nino et al.

(10) Patent No.: US 10,920,833 B2
(45) Date of Patent: Feb. 16, 2021

(54) GEARLESS TORQUE DRIVE

(71) Applicant: ECA Medical Instruments, Newbury Park, CA (US)

(72) Inventors: John Nino, Simi Valley, CA (US);
David Ivinson, Camarillo, CA (US);
David Tory, Simi Valley, CA (US)

(73) Assignee: ECA Medical Instruments, Newbury Park, CA (US)

( * ) Notice: Subject to any disclaimer, the term of this patent is extended or adjusted under 35 U.S.C. 154(b) by 0 days.

(21) Appl. No.: 15/946,284

(22) Filed: Apr. 5, 2018

(65) Prior Publication Data

US 2018/0223911 A1 Aug. 9, 2018

Related U.S. Application Data

(63) Continuation of application No. PCT/US2016/035707, filed on Jun. 3, 2016.
(Continued)

(51) Int. Cl.
*B25B 23/14* (2006.01)
*B25B 23/145* (2006.01)
(Continued)

(52) U.S. Cl.
CPC .............. *F16D 7/044* (2013.01); *A61B 17/00* (2013.01); *A61B 17/16* (2013.01);
(Continued)

(58) Field of Classification Search
CPC . B25B 23/141; B25B 23/1427; B25B 23/147; F16D 7/044; A61B 17/00; A61B 17/16; A61B 17/8875
(Continued)

(56) References Cited

U.S. PATENT DOCUMENTS 4,272,973 A * 6/1981 Fu-Tsai ................. B25B 23/141
464/23
4,311,224 A * 1/1982 Kato ....................... F16D 1/094
192/56.5
(Continued)

FOREIGN PATENT DOCUMENTS

EP         2556926 A2    2/2013
WO    WO 2009/129029 A1   10/2009
(Continued)

OTHER PUBLICATIONS

International Patent Application No. PCT/US2016/035707; Int'l Search Report and the Written Opinion; dated Sep. 8, 2016; 11 pages.
(Continued)

*Primary Examiner* — Orlando E Aviles
*Assistant Examiner* — Thomas Raymond Rodgers
(74) *Attorney, Agent, or Firm* — Ferguson Case Orr Paterson

(57) ABSTRACT

Torque-limiting mechanisms comprising an upper shank component with a torque-limiting interface, a lower shank component with a torque-limiting interface, and a biasing element. Torque-limiting interfaces having a plurality of undulations arranged around an axial bore or drive socket and separated by a plurality of transition regions, with each undulation having an upslope, a peak, and a downslope. The torque-limiting interfaces are configured to engage and disengage to provide torque transmission with predetermined torque limits at various rotational speeds and for amounts of actuations while remaining within a specified operational range.

20 Claims, 6 Drawing Sheets

Related U.S. Application Data

(60) Provisional application No. 62/238,359, filed on Oct. 7, 2015.

(51) Int. Cl.

| | | |
|---|---|---|
| *B25B 23/142* | (2006.01) | |
| *B25B 23/147* | (2006.01) | |
| *F16D 7/04* | (2006.01) | |
| *A61B 17/88* | (2006.01) | |
| *A61B 17/16* | (2006.01) | |
| *A61B 17/00* | (2006.01) | |
| *A61B 90/00* | (2016.01) | |

(52) U.S. Cl.
CPC ........ *A61B 17/8875* (2013.01); *B25B 23/141* (2013.01); *B25B 23/145* (2013.01); *B25B 23/147* (2013.01); *B25B 23/1427* (2013.01); *A61B 2017/0023* (2013.01); *A61B 2017/00398* (2013.01); *A61B 2090/031* (2016.02)

(58) Field of Classification Search
USPC .......................................................... 81/475
See application file for complete search history.

(56) References Cited

U.S. PATENT DOCUMENTS

| | | | | |
|---|---|---|---|---|
| 4,678,452 A * | 7/1987 | Nelson | ..................... | F16D 7/044 464/38 |
| 5,366,412 A * | 11/1994 | Beaty | ................... | A61C 8/0089 433/173 |
| 5,947,214 A * | 9/1999 | Tibbitts | ................... | E21B 17/04 175/276 |
| 6,082,941 A * | 7/2000 | Dupont | ................... | F16B 31/02 411/7 |
| 6,132,435 A * | 10/2000 | Young | ................ | A61B 17/8875 192/56.54 |
| 6,487,943 B1 | 12/2002 | Jansson | | |
| 6,948,410 B1 * | 9/2005 | Larson | ................ | B25B 23/1427 173/176 |
| 7,025,151 B2 * | 4/2006 | Hehli | ................. | A61B 17/8875 173/176 |
| 7,243,581 B1 * | 7/2007 | Gao | ...................... | B25B 23/141 192/38 |
| 7,938,046 B2 | 5/2011 | Nino | | |
| 8,083,596 B1 * | 12/2011 | Silver | ...................... | F16D 7/10 464/31 |
| 8,359,955 B2 * | 1/2013 | Deneault | ............... | B25B 15/001 81/473 |
| 8,365,641 B2 * | 2/2013 | Daglow | ............. | B25B 23/1427 81/467 |
| 9,731,407 B1 * | 8/2017 | Edmisten | ............ | B25B 23/1427 |
| 2005/0284648 A1 * | 12/2005 | Frauhammer | ......... | B25B 23/141 173/176 |
| 2006/0016300 A1 | 1/2006 | Bubei | | |
| 2009/0102276 A1 * | 4/2009 | Mercat | ................... | B62K 25/02 301/124.2 |
| 2009/0164017 A1 * | 6/2009 | Sommerich | ............... | A61F 2/44 623/17.16 |
| 2013/0048460 A1 * | 2/2013 | Keller | ................... | B25B 23/141 192/56.61 |
| 2013/0305889 A1 * | 11/2013 | Nino | ...................... | B25B 15/04 81/475 |
| 2014/0000420 A1 | 1/2014 | Chuang | | |
| 2014/0123819 A1 * | 5/2014 | Beemer | ................ | B25B 23/142 81/476 |
| 2014/0276893 A1 * | 9/2014 | Schaller | ............. | B25B 23/0042 606/104 |
| 2015/0151416 A1 | 6/2015 | Chen | | |
| 2015/0252884 A1 * | 9/2015 | Serkh | ...................... | F16H 55/36 474/94 |

FOREIGN PATENT DOCUMENTS

| | | |
|---|---|---|
| WO | WO 2014/116414 A1 | 7/2014 |
| WO | 2017062068 | 4/2017 |

OTHER PUBLICATIONS

International Patent Application No. PCT/US2016/035707; Int'l Preliminary Report on Patentability; dated Apr. 19, 2018; 8 pages.
European Patent Application No. 16854016.9; Extended Search Report; dated Jun. 26, 2019; 8 pages.
Search Report and Written Opinion of International Patent Application No. PCT/US2016/035711; dated Sep. 19, 2016; 15 pages.
Preliminary Report on Patentability of International Patent Application No. PCT/US2016/035711; dated Apr. 19, 2018; 12 pages.

* cited by examiner

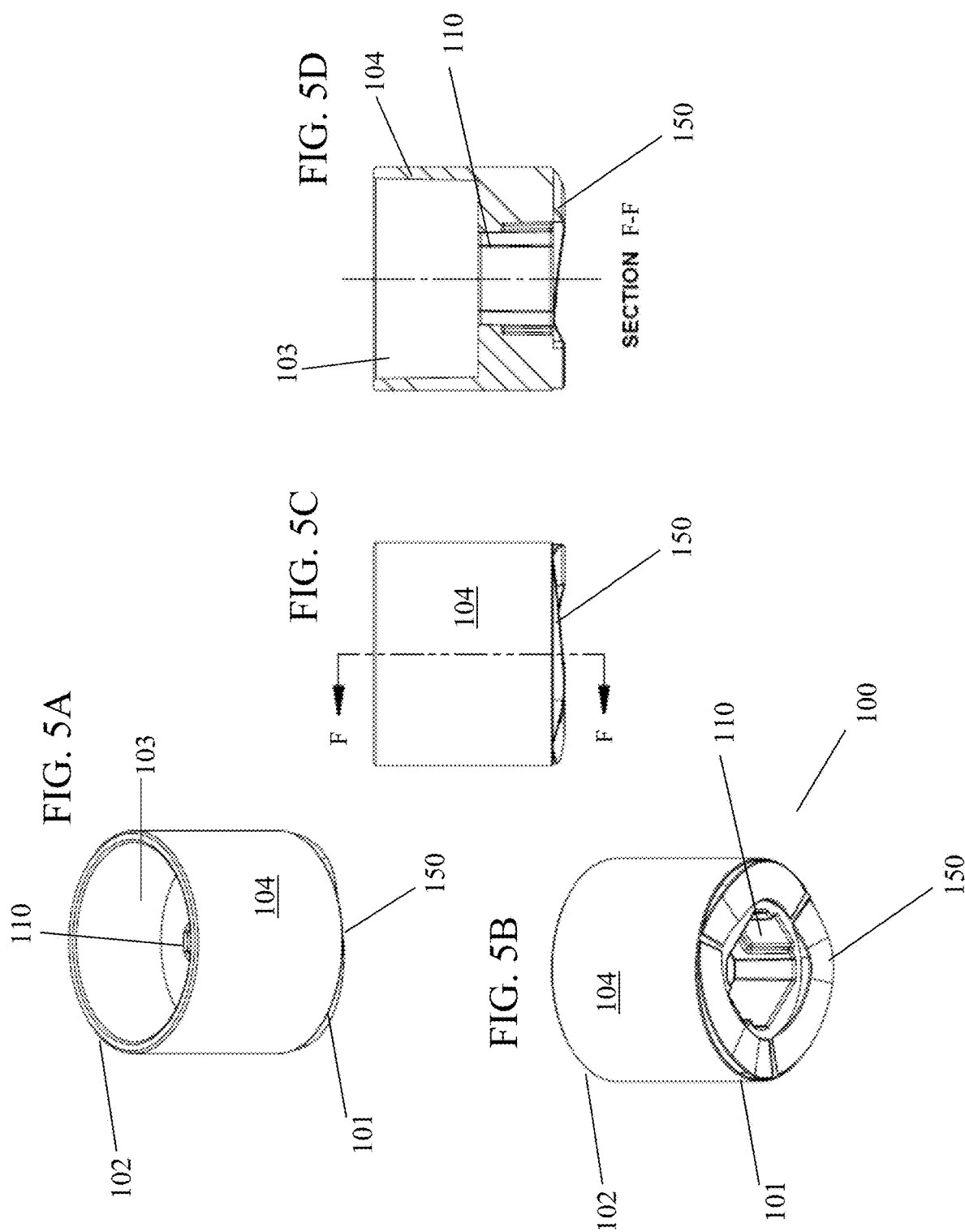

Time [Seconds]

GEARLESS TORQUE DRIVE

CROSS REFERENCE

This application is a continuation of International Patent Application PCT/US2016/035707 filed Jun. 3, 2016, which claims priority to U.S. Provisional Patent Application 62/238,359 filed Oct. 7, 2015, the contents of which are incorporated herein by reference as if fully set forth herein.

BACKGROUND

1. Field

This disclosure relates to gearless torque drives for torque-limiting devices that are suitable for operation at high rotational speeds.

2. General Background

Torque is a measure of force acting on an object that causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N-m). The joule, which is the SI unit for energy or work, is also defined as an N-m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch-pounds.

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely. Such reusable devices also require sterilization.

Disposable drivers are an alternative to the reusable drivers. Once the driver has been used, it is discarded.

Disposable drivers are traditionally used for low torque applications. The standard torque values in these applications typically range from about 4 to about 20 inch-ounces. It has, however, been a challenge to develop a reliable disposable driver capable of imparting higher torques for larger applications.

Power tools are used for some applications in the medical industry. Such power tools can provide torque to a workpiece while also providing higher rotational rates than can be provided with manually driven tools. Torque-limiting systems can be utilized with medical power tools, either as an additional attachment provided in-line between the power tool and the workpiece or as internalized systems within the power tool itself. Reusable torque-limiting systems need to be sterilized between uses and typically must be serviced and recalibrated periodically to ensure performance within specifications. Disposable torque-limiting systems are an alternative to the reusable systems. Once the torque-limiting system has been used, it is discarded.

Disposable torque limiting devices which are inexpensive for use with power tools can fall out of specification with increased RPMs and as such fail to perform sufficiently.

Thus there is a need for disposable torque-limiting systems that can be utilized with medical power tools to limit applied torque at higher rotational speeds and remain in specification over a predetermined number of actuations. The disclosure is directed to these and other important needs.

SUMMARY

This disclosure provides torque-limiting mechanisms comprising an upper shank component, a lower shank component, and a biasing element. The upper shank component comprises an upper shank component comprising a proximal end, a distal end, an axial bore connecting the proximal end and the distal end, and a first torque-limiting interface disposed on the proximal end. The lower shank component comprising a proximal end, a distal end, a drive socket connecting the proximal end and the distal end, and a second torque-limiting interface disposed on the proximal end, wherein the upper shank component and the lower shank component are aligned along an axis in the direction of the axial bore and the drive socket with the first torque-limiting interface in contact with the second torque-limiting interface. The biasing element is configured to apply compressive force along the axis to compress the first torque-limiting interface against the second torque-limiting interface. The upper shank component and the lower shank component are configured to engage to rotate together when torque is applied to the lower shank component via the drive socket. The upper shank component and the lower shank component are configured to disengage when a predetermined torque limit is exceeded.

This disclosure provides torque-limiting interfaces comprising a plurality of undulations arranged around an axial bore or drive socket and separated by a plurality of transition regions. Each undulation comprises an upslope, a peak, and a downslope. The inclination angle of each upslope can be about 3 to about 15 degrees, about 5 to about 9 degrees, about 6 to about 8 degrees, or about 7 degrees. The declination angle of each downslope can be about 5 to about 45 degrees, more preferably about 10 to about 30 degrees, more preferably about 10 to about 20 degrees, and most preferably about 15 degrees.

DRAWINGS

The above-mentioned features of the present disclosure will become more apparent with reference to the following description taken in conjunction with the accompanying drawings wherein like reference numerals denote like elements. In addition, the drawings are not necessarily drawn to scale. In the drawings.

Figure 6A:
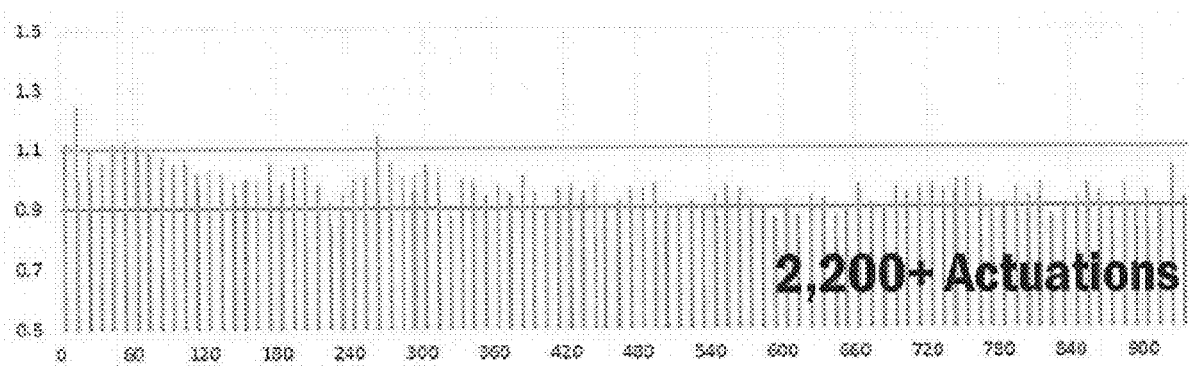
Figure 6B:
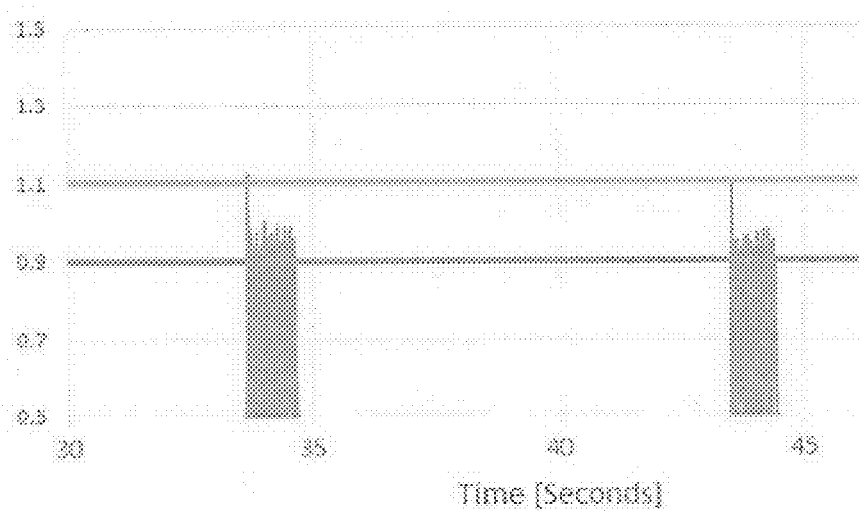
Figure 6C:
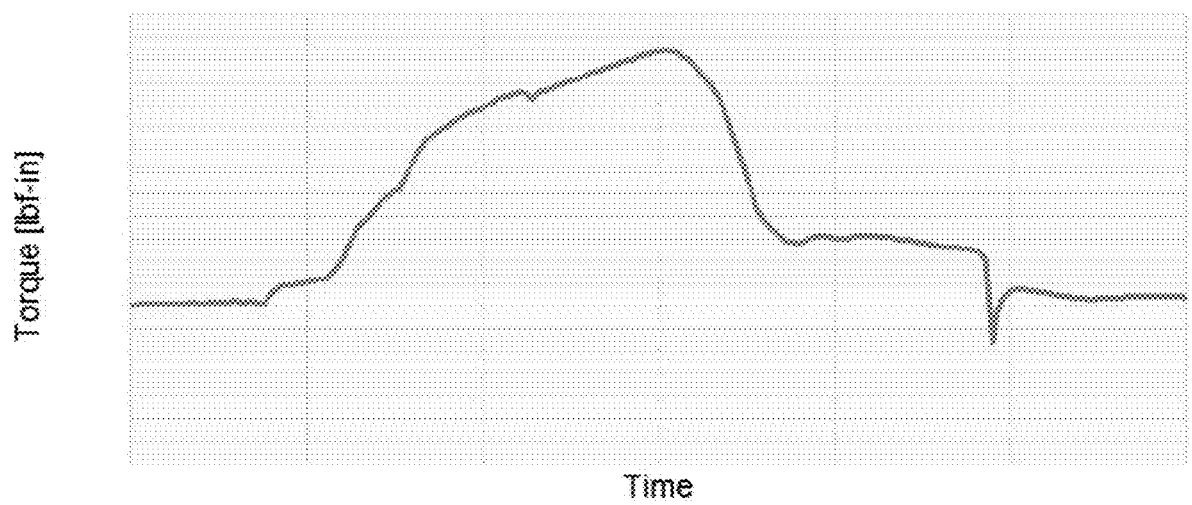
Figure 6D:
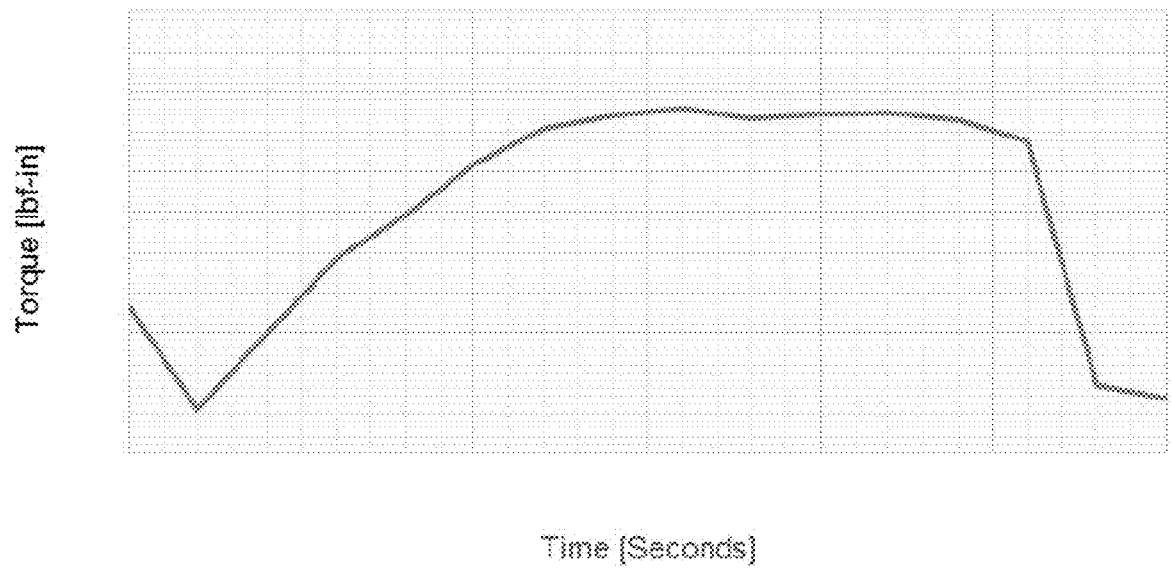

FIGS. 5A and 5B show perspective views of some aspects of components of torque-limiting mechanisms of the present disclosure. FIG. 5C shows a side view of some aspects of components of torque-limiting mechanisms of the present disclosure. FIG. 5D shows a cut-away section view along the section marked F-F in FIG. 5C;

FIGS. 6A and 6B show testing data from testing of an implementation of the torque-limiting mechanisms of the present disclosure;

FIG. 6C shows testing data from testing of a prior art torque-limiting mechanism; and FIG. 6D shows testing data from testing of an implementation of the torque-limiting mechanisms of the present disclosure.

As shall be appreciated by those having ordinary skill in the art, the figures are not to scale, and modifications to scale within a figure or across the figures are considered within the present disclosure.

FURTHER DESCRIPTION

Figure 1:
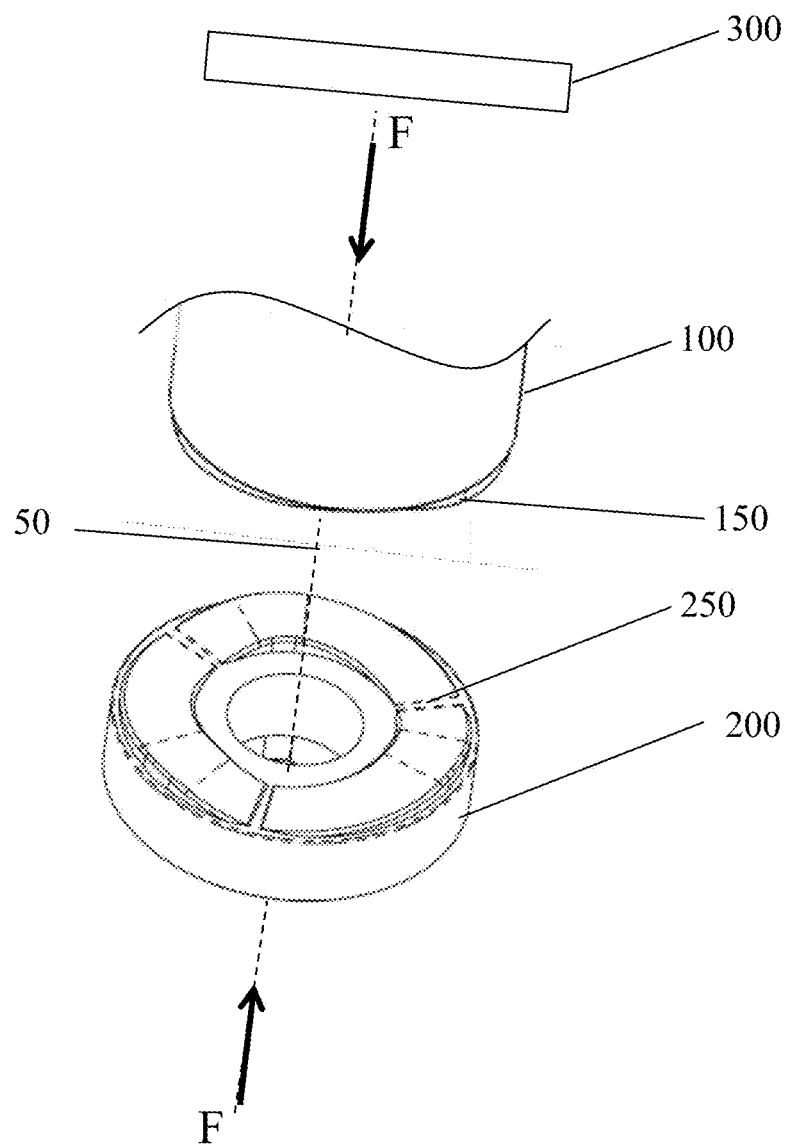
FIG. 1 shows an exploded assembly perspective view of some aspects of torque-limiting mechanisms of the present disclosure.
Figure 2:
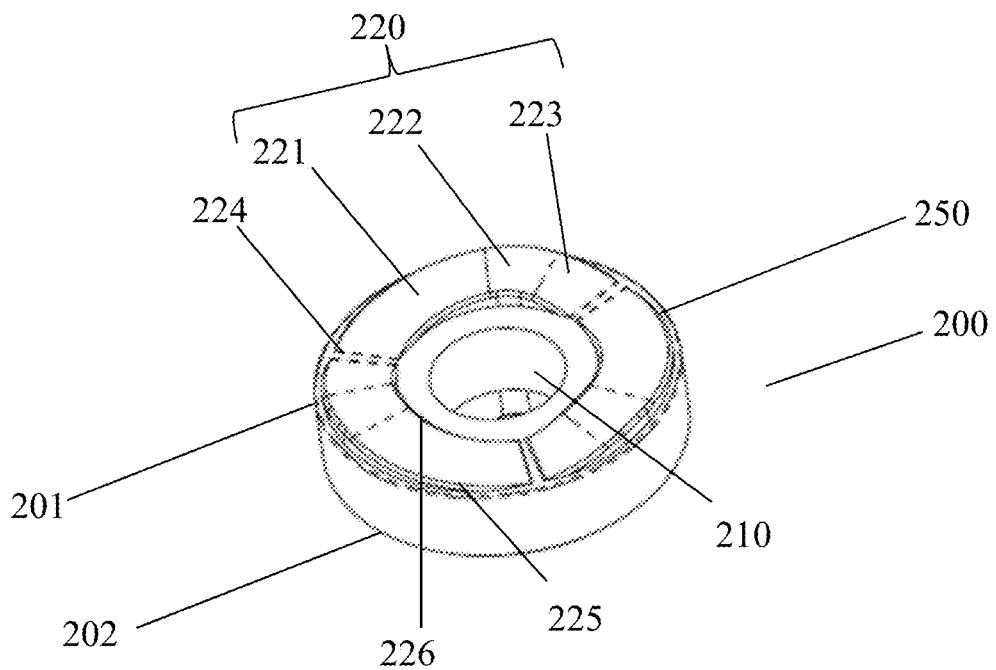
FIG. 2 shows a perspective view of some aspects of components of torque-limiting mechanisms of the present disclosure.
Figure 3:
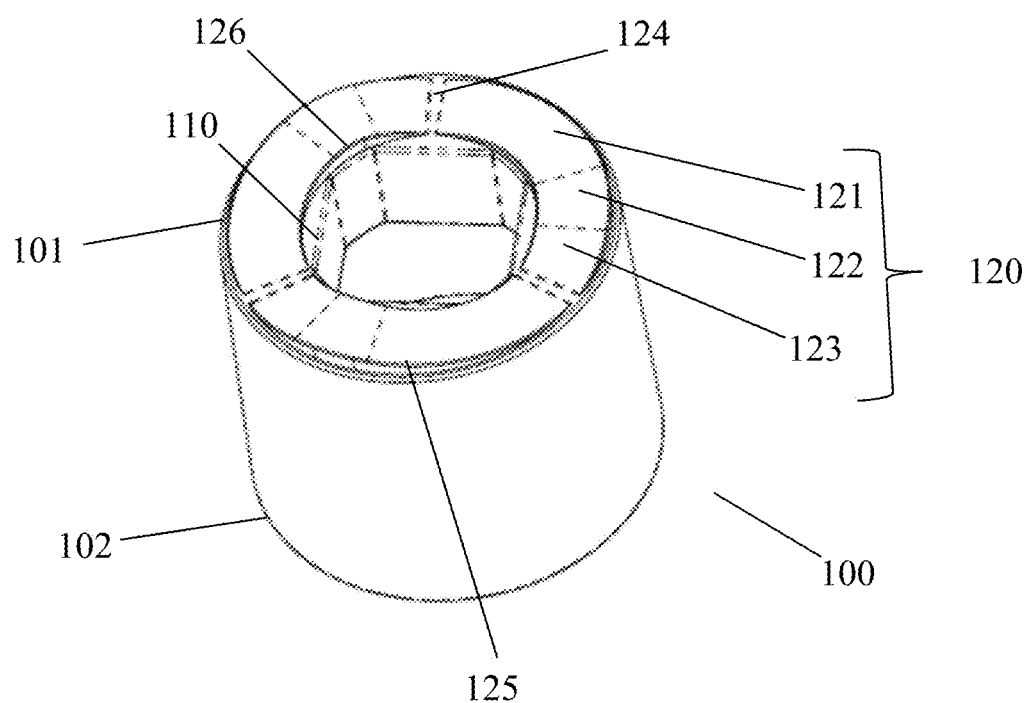
FIG. 3 shows a perspective view of some aspects of components of torque-limiting mechanisms of the present disclosure.

FIGS. 1, 2, and 3 shows some aspects of some implementations of torque-limiting mechanisms of the present disclosure. The torque-limiting mechanisms can have an upper shank component 200, a lower shank component 100, and a biasing element 300 (not shown) configured to apply a force (F) along an axis 50. Upper shank component 200 can have a proximal end 201, a distal end 202, an axial bore 210 connecting the proximal end and the distal end, and a torque-limiting interface 250 disposed on the proximal end. Lower shank component 100 can have a proximal end 101, a distal end 102, a drive socket 110 connecting the proximal end and the distal end, and a torque-limiting interface 150 disposed on the proximal end. The upper shank component and the lower shank component are aligned along an axis 50 in the direction of the axial bore 210 and the drive socket 110 with the torque-limiting interface 250 in contact with the torque-limiting interface 150. The biasing element 300 is configured to apply a compressive force (F) along the axis to compress the torque-limiting interface against the torque-limiting interface. The upper shank component 200 and the lower shank component 100 are configured to engage to rotate together when torque is applied to the lower shank component via the drive socket and are configured to disengage when a predetermined torque limit is exceeded. When disengaged, the torque-limiting interfaces 150/250 slide past each other in relative rotation about the axis 50. Drive socket 110 can have any suitable shape that allows for the transmission of torque to the lower shank component 100. Suitable shapes for the drive socket 110 include geometric shape profiles such as hexagons, squares, or truncated/rounded versions thereof.

Those of ordinary skill in the art can appreciate that the torque-limiting mechanisms of the present disclosure can be incorporated into any systems or devices that require torque-limited rotation between subcomponents of those systems or devices. In some implementations, the torque-limiting mechanisms of the present disclosure can be incorporated into torque-limited drivers for use in surgical applications; such drivers can be hand-driven or driven with power tools at higher rates of rotation.

FIGS. 2 and 3 show further aspects of some implementations. Upper shank component 200 can have a torque-limiting interface 250 with a plurality of undulations 220 arranged around the axial bore and separated by a plurality of transition regions 224. The lower shank component 100 can shave a torque-limiting interface 150 having a plurality of undulations 120 arranged around the drive socket and separated by a plurality of transition regions 124, the first and second pluralities being equal in number. Each undulation 120/220 can be formed as an upslope 121/221, a peak 122/222, and a downslope 123/223.

In some implementations, the torque-limiting interfaces 150/250 do not contain any step or drop-off greater than about 0.005". One or more cutouts or slots (not shown) can be provided in one or more of the upslopes, 121/221 peaks 122/222, or downslopes 123/223 to collect at least a portion of any debris generated during operation. In some embodiments, downslope 123/223 is designed with maximum length to provide the softest downward angle back down to the initial height of the next upslope 121/221. During powered rotation, a softer downslope mitigates degradation of the downslope 123/223 material. Such degradation adversely impact performance as the torque-limit at which disengagement occurs can change as the material degrades.

Each undulation 120/220 sweeps through a portion of the 360 degrees around the central axial bore 210 or drive socket 110, with the plurality of undulations 120/220 covering a total portion of the 360 degrees around the central axial bore. In some implementations, the total portion covered by the plurality of undulations 120/220 can be at least about 65% of the 360 degrees (about 235 degrees), at least about 70% of the 360 degrees (about 255 degrees), at least about 80% of the 360 degrees (about 285 degrees), at least about 83% of the 360 degrees (about 300 degrees), at least about 90% of the 360 degrees (about 324 degrees), at least about 95% of the 360 degrees (about 345 degrees), or at least about 98% of the 360 degrees (about 350 degrees). The portion not covered by the plurality of undulations 120/220 is filled with transition regions 124/224 between the end of each downslope 123/223 and the beginning of the next upslope 121/221. Each transition region 124/224 can be selected to be no greater than about 35 degrees, no greater than about 20 degrees, no greater than about 15 degrees, no greater than about 10 degrees, no greater than about 5 degrees, no greater than about 4 degrees, no greater than about 3 degrees, no greater than about 2 degrees, no greater than about 1 degree, or can be eliminated entirely if the end of each downslope 123/223 is immediately adjacent to the beginning of the next upslope 121/221.

A softer downslope angle the torque-limiting interfaces 150/250 can substantially mitigate or eliminate any "click" or audible indication that the upper shank component 200 and lower shank component 100 have slipped past each other during a disengagement, also referred to herein as an actuation, when the predetermined torque limit has been exceeded. In some implementations, an actuation indicating system can be incorporated in the overall torque-limiting driver to create one or more "clicks" when the upper shank component 200 and lower shank component 100 have slipped past each other. In some implementations, the actuation indicating system can include a flag feature on either lower shank component 100 or upper shank component 200 that impacts one or more spokes, protrusions, or other physical features on another component in the system as relative rotation occurs.

Upper shank component 200 and lower shank component 100 can be formed from various materials. Suitable materials include stainless steels, aluminums, plastic materials, or composites including plastic. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like as well as blends or mixtures thereof. In some implementations, 30% glass-filled polyetherimide can be used to form one or more of the above components. For components formed from stainless steels or aluminums, the shank components can be heat treated, passivated, or anodized via suitable methods known to those of ordinary skill in the art. In some implementations, aluminum shank components can be finished with a hard anodize finish per MIL-A-8625F, type III, class 2. In some implementations, stainless steel 440*c* shank components can be heat treated per AMS 2759/5D to 58Rc and passivated with treatment with nitric acid and/or sodium dichromate. Other heat treatments and passivation methods known in the art are also suitable. In some implementations, corresponding pairs of gear rings are formed from different materials. In some preferred implementations, one shank component 100/200 is formed from stainless steel or aluminum and the corresponding gear ring is formed from 30% glass-filled polyetherimide (PEI) resin. In some implementations the shank components 100/200 can be made from the same material.

According to aspects of one or more exemplary implementations, components of the torque-limiting mechanisms of the present disclosure are resistant to sterilization, cleaning, and preparation operations. For example, the upper shank component and lower shank component may be configured to withstand sterilization by methods including radiation (e.g., gamma rays, electron beam processing), steam (e.g., autoclave), detergents, chemical (e.g., Ethylene Oxide), heat, pressure, inter alia. For example, materials may be selected according to resistance to one or more selected sterilization techniques.

The material selection and surface treatments applied to the torque-limiting interfaces 150/250 can affect the predetermined torque limit. The static friction between the torque-limiting interfaces 150/250 determines when disengagement will occur, as the rotation force can overcome the static friction holding the interfaces into engagement with each other. Greater contact surface area of the opposing interfaces, via wider undulations 120/220 or other aspects of the shape/profile of the undulations 120/220, will increase the resistance to actuation and lead to a higher predetermined torque limit.

In some preferred implementations, upper shank component 200 and lower shank component 200 are both mad from 30% glass-filled polyetherimide (PEI) resin. In some implementations, a glass-filled ULTEM® PEI from Saudi Basic Industries Corporation (SABIC) can be used to form the upper shank component 200 and lower shank component 200 via machining or molding. In some implementations, a lubricant is disposed on one or both of torque-limiting interfaces 150/250. Such lubricants are useful to avoid excessive heat build-up during actuations at high rates of rotation, which can melt or degrade the PEI material.

Figure 4E:
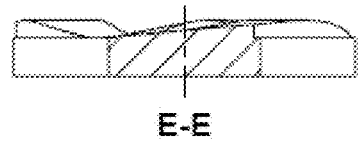
FIGS. 4B, 4C, 4D, 4E, and 4F show cut-away sectional views along the sections marked A-A, B-B, C-C, D-D, and E-E in FIG. 4A.
Figure 4A:
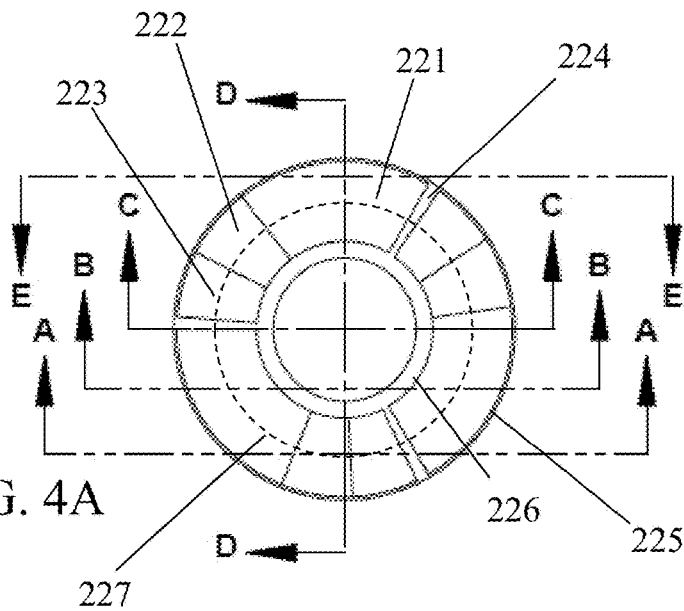
FIG. 4A shows a top view of some aspects of components of torque-limiting mechanisms of the present disclosure.
Figure 4F:
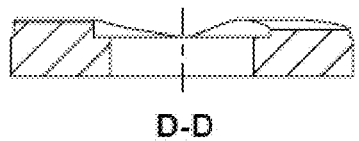
Figure 4B:
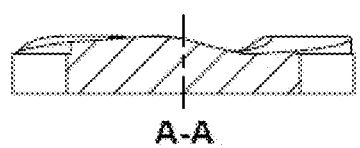
Figure 4C:
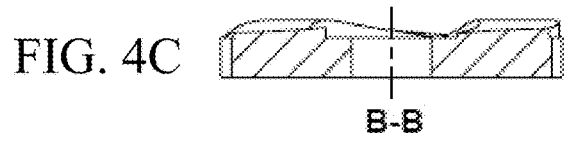
Figure 4D:
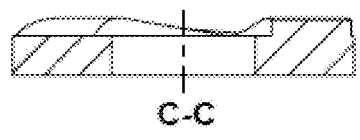

The shape of some implementations of undulations 120/220 can be seen in FIGS. 4A-4F. FIG. 4A shows a top view of the torque-limiting interface 150 at the proximal end 201 of upper shank component 200. FIG. 4B shows a cut-away view of the upper shank component 200 along line A-A shown in FIG. 4A. FIG. 4C shows a cut-away view of the upper shank component 200 along line B-B shown in FIG. 4A. FIG. 4D shows a cut-away view of the upper shank component 200 along line C-C shown in FIG. 4A. FIG. 4E shows a cut-away view of the upper shank component 200 along line E-E shown in FIG. 4A. FIG. 4F shows a cut-away view of the upper shank component 200 along line D-D shown in FIG. 4A. The number of undulations 120/220 is determined by the size of the upper shank component 200 and lower shank component 100 and the shape of the undulations 120/220. The size of the shank components 100/200 determines the functional path length that the plurality of undulations may have. The functional path length refers to the circumferential length of a circular path along the midpoint of the undulations, shown as a dashed circle 227 in FIG. 4A. A larger diameter shank component allows for a larger functional path length. The shape of the undulations 120/220 refers to the inclination angle of the upslope 121/221, the length of the peak 122/222, and the declination angle of the downslope 123/223. Sharper inclination and declination angles and shorter peak lengths can lead to a shorter functional path length for each individual undulation, which would allow for more undulations to be placed onto the torque-limiting interfaces 150/250. The torque-limiting interfaces may have two undulations, three undulations, four undulations, or five or more undulations. Three or more undulations are used in some preferred implementations, as systems with only two undulations may be less stable during actuations at higher rates of rotation.

The width of the undulations can span the entirety of the annular ring of the proximal ends of the upper shank component and lower shank component between the drive socket 110 or axial bore 210 and outer edges of those components, or can be reduced widths to accommodate adjoining parts to avoid undesired contact points or friction. The width must be sufficient to provide adequate interface contact area with the opposing set of waves to create the friction necessary for torque transmission. Larger widths allow for the applied force to be distributed over larger surface areas and reduce stress on the components.

The inclination angle of each upslope 121/221 can be about 3 to about 15 degrees, more preferably about 5 to about 9 degrees, more preferably about 6 to about 8 degrees, and most preferably about 7 degrees. The inclination angle is measured along the functional path length along the midpoint of the undulations, as the angle along the interior edge 126/226 will be higher due to the shorter path length, and the angle along the exterior edge 125/225 will be lower due to the longer path length. The declination angle of each downslope 123/223 can be about 5 to about 45 degrees, more preferably about 10 to about 30 degrees, more preferably about 10 to about 20 degrees, and most preferably about 15 degrees. The declination angle is measured along the functional path length along the midpoint of the undulations. In some preferred implementations, the ratio of the functional path length of the upslope 121/221 of each undulation to the functional path length of the downslope of each undulation can be about 3.0:1, about 2.5:1, about 2.4:1, about 2.3:1, about 2.2:1, about 2.1:1, about 2.0:1, about 1.9:1, about 1.8:1, about 1.7:1, about 1.6:1, about 1.5:1, about 1.4:1, about 1.3:1, about 1.2:1, about 1.1:1, or about 1.0:1. In some preferred implementations the ratio can be between about 2.2:1 and about 1.8:1, or more preferably about 2.0:1.

Each peak 122/222 has an even height across its surface from the interior edge 126/226 to the exterior edge 125/225 at each radial line from the central axis of the respective shank component 100/200. In some implementations the functional path length of each peak 122/222 is approximately equal to the length of each of the transition regions 124/224, such that the peaks 122/222 of each torque-limiting interface are complementary and mate with the transition regions 124/224 of the opposing torque-limiting interface.

FIGS. 5A-5D show some aspects of an implementation of a lower shank component 100 the present disclosure. FIG. 5A and FIG. 5B show perspective views of an implementation of a lower shank component 100. FIG. 5C shows a side view while FIG. 5D shows a cross-sectional view along the line D-D shown in FIG. 5C. The lower shank component 100 can include a retaining cavity 103 configured to retain biasing element 300 (not shown) within a wall 104 located at the distal end 102. The retaining cavity 103 provides for a volume in which a biasing element 300 can be compressed, so that if biasing element 300 expands radially during compression it will be retained within retaining cavity 103 rather than impinging or contacting other components within the system.

Biasing element 300 provides compressive force between the upper shank component and lower shank component to place the torque-limiting interfaces 150/250 into frictional contact with each other. Suitable biasing elements can include springs, spring washers, also referred to as Belleville washers, grommets or washers of compressible materials such as rubber. In some implementations, compressible materials with durometer ratings between about 50 durometer and 100 durometer can be used as biasing elements. The biasing element 300 can be compressed by other components in a torque-limiting driver. The amount of compression applied to a biasing element can be used to set the predetermined torque limit at which disengagement/actuation of the torque-limiting mechanism occurs. Higher compressive forces created by the biasing element will create higher predetermined torque limits.

According to aspects of one or more exemplary implementations, the torque-limiting mechanisms of the present disclosure are capable of imparting torques of up to about 6 N-m at various rotational speeds. For example, the torque output range may be selected between about 0.5 N-m and about 6 N-m and utilized in combination with a rotational speed selected between about 150 RPMs and about 1300 RPMs. Typically, the torque requirement is different for different operations and for different implants. For example, applications may include those in the field of orthopedic surgery, construction and emplacement of implants, etc. In such instances, the predetermined torque limit may be about 6 N-m, depending on an implant's specifications. Smaller fasteners may utilize lower torque limits between about 0.1 N-m and about 2.0 N-m. In some instances the torque-limiting mechanisms of the present disclosure will provide a predetermined torque of at least one of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 Newton-meters (N-m) of torque at a rotational speed of at least one of 50, 100, 150, 200, 250, 300, 350, 400, 450, 500, 550, 600, 650, 700, 750, 800, 850, 900, 950, 1000, 1050, 1100, 1150, 1200, 1250, or 1300 RPMs over at least one of 5, 10, 20, 30, 40, 50, 60, 70, 80, 90, 100, 105, 110, 120, 150, 180, 200, 220, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 actuations while remaining within a specified operational range.

FIGS. 6A and 6B show testing data of an implantation of a torque-limiting mechanism of the present disclosure. A torque-limiting driver that incorporated a torque-limiting mechanism having the torque-limiting interfaces shown in FIGS. 2, 3, and 4A-4F formed from 30% glass-filled PEI resin was assembled and tested at 450 RPM with a predetermined torque limit of about 1.05 N-m. The torque-limiting driver was rotated at 450 RPM for 1 second intervals and the torque output was measured with an electronic torque transducer. FIG. 6A shows that the torque limit remained within an operational range of about 0.9 to about 1.1 N-m over approximately 2,200 actuations. FIG. 6B shows data for two 1-second intervals and shows the actuations that occur over those 1-second intervals. Approximately 22 actuations, from 7.5 revolutions per second at 450 RPM, occur in each 1-second interval, with the applied torque remaining within the operational range.

FIGS. 6C and 6D show the torque output profiles of torque-limiting drivers over a single hand-driven actuation. FIG. 6C shows the torque profile of a traditional crown gear interface with opposing sets of jagged teeth, such as that disclosed in U.S. Pat. No. 7,938,046, incorporated herein in its entirety for all purposes. The resulting profile shows a spike drop-off in torque as the opposing teeth slip off each other sharply. Systems incorporating these jagged teeth crown gears exhibit inconsistent torque-limits across ranges of rotational speeds, with higher rotational speeds showing higher torque. In contrast, FIG. 6D shows a torque output profile from the system used in FIGS. 6A and 6B, which incorporates the three-undulation torque-limiting interfaces shown in FIGS. 2, 3, 4A-4F and described more fully elsewhere herein. The torque output increases and decreases more gradually and smoothly through each actuation, which provides for a more consistent torque-limit across rotational speeds, including higher rotational speeds up to 1300 RPM. Further, the torque-limiting mechanisms are more durable and can last through a higher number of actuations, including over 2,000 actuations, while remaining within a specified operational range.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A torque-limiting mechanism comprising:
   an upper shank component comprising a proximal end, a distal end, an axial bore connecting the proximal end and the distal end, and a first undulated torque-limiting interface disposed on the proximal end;
   a lower shank component comprising a proximal end, a distal end, a drive socket disposed between the proximal end and the distal end, and a second undulated torque-limiting interface disposed on the proximal end, wherein the upper shank component and the lower shank component are aligned along an axis in the direction of the axial bore and the drive socket with the first torque-limiting interface in contact with the second torque-limiting interface; and
   a compressible biasing element with a 50 to 100 durometer rating configured to apply compressive force (F) along the axis to compress the first torque-limiting interface against the second torque-limiting interface;
   wherein the upper shank component and the lower shank component are configured to engage to rotate together when torque is applied to the lower shank component via the drive socket; and,
   wherein the upper shank component and the lower shank component are configured to disengage when a predetermined torque limit is exceeded,
   the first torque-limiting interface comprises a first plurality of non-metallic undulations arranged around the axial bore and separated by a first plurality of transition regions;
   the second torque-limiting interface comprises a second plurality of non-metallic undulations arranged around the drive socket and separated by a second plurality of transition regions; and
   each undulation comprises an upslope, a peak, and a downslope, wherein each downslope has a declination angle of between 5 and 30 degrees such that degradation is mitigated between the first and second pluralities of undulations.

2. The torque-limiting mechanism of claim 1, wherein: the first and second pluralities are equal in number.

3. The torque-limiting mechanism of claim 1, wherein: each upslope has an inclination angle between 3 degrees and 15 degrees.

4. The torque-limiting mechanism of claim 1, wherein: each upslope has an inclination angle between 5 degrees and 9 degrees.

5. The torque-limiting mechanism of claim 1, wherein: each upslope has an inclination angle between 6 degrees and 8 degrees.

6. The torque-limiting mechanism of claim 1, wherein: each upslope has an inclination angle of 7 degrees.

7. The torque-limiting mechanism of claim 1, wherein the predetermined torque limit is between 0.1 Newton-meter and 3.0 Newton-meter.

8. The torque-limiting mechanism of claim 1, wherein the predetermined torque limit is between 3.0 Newton-meter and 6.0 Newton-meter.

9. The torque-limiting mechanism of claim 2 wherein the first torque-limiting interface and second torque-limiting interface each comprise three undulations.

10. The torque-limiting mechanism of claim 2 wherein the first torque-limiting interface and second torque-limiting interface each comprise four undulations.

11. The torque-limiting mechanism of claim 2 wherein the first torque-limiting interface and second torque-limiting interface each comprise five undulations.

12. The torque-limiting mechanism of claim 1 wherein the torque-limiting mechanism provides a predetermined torque between 0.1 Newton-meter and 6 Newton-meters of torque at a rotational speed between 50 RPM and 1300 RPM over at least one of 5, 10, 20, 30, 40, 50, 60, 70, 80, 90, 100, 105, 110, 120, 150, 180, 200, 220, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, or 2500 actuations while remaining within a specified operational range.

13. The torque-limiting mechanism of claim 1, wherein each downslope has a declination angle of between 10 and 30 degrees.

14. The torque-limiting mechanism of claim 13, wherein each downslope has a declination angle of between 10 and 20 degrees.

15. The torque-limiting mechanism of claim 14, wherein each downslope has a declination angle of 15 degrees.

16. The torque-limiting mechanism of claim 1, wherein each upslope has a functional path length defined along a midpoint of each undulation, each downslope has a functional path length defined along the midpoint of each undulation, and the ratio of the functional path length of the upslope to the functional path length of the downslope is between 2.2:1 and 1.8:1.

17. The torque-limiting mechanism of claim 1, wherein the lower shank component includes a retaining cavity configured to receive the compressible biasing elements, such that the compressible biasing element is retained within the retaining cavity when the compressible biasing element is compressed to expand radially.

18. The torque-limiting mechanism of claim 2, wherein each peak has a length between an adjacent upslope ad an adjacent downslope, each transition region has a length between an adjacent upslope and an adjacent downslope, and the length of the peak is equal to the length of the transition region.

19. The torque-limiting mechanism of claim 1, wherein the ratio of the first plurality of undulations arranged around the axial bore to the first plurality of transition regions is at least 65:35, and wherein the ratio of second plurality of undulations arranged around the drive socket to the second plurality of transition regions is at least 65:35.

20. The torque-limiting mechanism of claim 1, further comprising an actuation indicating system configured to create an audible indication when the upper shank component and the lower shank component have slipped past each other.

* * * * *